United States Patent [19]

Scharnweber et al.

[11] Patent Number: 5,723,038
[45] Date of Patent: Mar. 3, 1998

[54] PROCESS FOR PRODUCING A GRADIENT COATING MADE OF CALCIUM PHOSPHATE PHASES AND METAL OXIDE PHASE ON METALLIC IMPLANTS

[75] Inventors: Dieter Scharnweber; Henrike Bersch; Hartmut Worch, all of Dresden, Germany; Jurgen Hofinger, Gubener Strasse 28, D-01237 Dresden, Germany; Curt Kranz, Berlin; Wolfgang Pompe, Kurort Hartha, both of Germany

[73] Assignee: Jurgen Hofinger, Dresden, Germany

[21] Appl. No.: 718,445

[22] PCT Filed: Feb. 6, 1996

[86] PCT No.: PCT/DE96/00197

§ 371 Date: Dec. 2, 1996

§ 102(e) Date: Dec. 2, 1996

[87] PCT Pub. No.: WO96/24391

PCT Pub. Date: Aug. 15, 1996

[30] Foreign Application Priority Data

Feb. 10, 1995 [DE] Germany ............ 195 04 386.3

[51] Int. Cl.$^6$ .................... C25D 9/04; A61L 27/00
[52] U.S. Cl. .................. 205/107; 205/318; 623/901
[58] Field of Search ................. 205/107, 318; 623/16, 901

[56] References Cited

U.S. PATENT DOCUMENTS

| 4,478,689 | 10/1984 | Loch | 204/14.1 |
| 4,666,567 | 5/1987 | Loch | 204/14.1 |
| 5,310,464 | 5/1994 | Redepenning | 205/318 |
| 5,354,390 | 10/1994 | Haszmann et al. | 148/518 |

FOREIGN PATENT DOCUMENTS 2073781  1/1994  Canada.

Primary Examiner—Kathryn L. Gorgos
Assistant Examiner—William T. Leader
Attorney, Agent, or Firm—Griffin, Butler, Whisenhunt & Kurtossy

[57] ABSTRACT

The invention concerns a process for producing a gradient coating of calcium phosphat phases and metal oxide phases on metallic implants, in particular made of titanium or titanium alloys, for use as dental, jaw or joint implants. A solution containing calcium ions and phosphate ions is used as electrolyte of which the pH is slightly acidic to approximately neutral. The substrate electrodes are alternately polarized cathodically and anodically. The layer deposited in a gratuated manner is adherent, has a fine structure and is distinguished by a high degree of biocompatibility.

9 Claims, No Drawings

PROCESS FOR PRODUCING A GRADIENT COATING MADE OF CALCIUM PHOSPHATE PHASES AND METAL OXIDE PHASE ON METALLIC IMPLANTS

This is a national stage application of PCT/DE96/00197, filed Feb. 6, 1996.

The invention refers to a process for producing a gradient coating containing calcium phosphate phases and metal oxide phases on metallic implants, especially on titanium or titanium alloys, for use as dental, maxillofacial or joint implants.

It is well known that the time of ingrowth of an metallic implant until the full mechanical loadability is achieved can be reduced if the metallic implants have been coated with calcium phosphate phases especially with hydroxyapatite, a calcium phosphate phase similiar to bone.

The connection between metal implant and calcium phosphate can be realized in different ways. According to EP-A 0006544, spherical calcium phosphate particles arc molded into a model together with the implant material. In U.S. Pat. No. 4,145,764 a process is described, in which ceramic particles are thermically sprayed on an implant. However, these techniques are very energy intensive, expensive and time consuming. Furthermore, from EP 0232791 and EP 0237053 processes are known, in which a resorbable calcium phosphate ceramic is deposited on titanium by means of an anodic oxidation under spark discharge in an aqueous electrolyte solution. However, the so produced coating does not consist of hydroxyapatite or fluorapatite but of oxides and strongly resorbable calcium phosphate phases. With a complete resorption of the calcium phosphate phases also the bioactive character of the implant is lost.

DE 43 03 575 C1 describes a process for producing a patite coatings on metal implants by inducing a plasma-chemical reaction by means of alternating current in aqueous solutions. An electrolyte solution is used made from the salts of alkali or alkaline earth metals, in which hydroxyapatite and/or fluorapatite is dispersed with a defined grainsize and concentration. The plasma-chemical process leads to coatings, which consist of pure hydroxyapatite or fluorapatite to an extent of up to 95%.

Disadvantages of this process are especially the large thickness of the coating (up to 250 µm) as well as the come graining of the coating (up to 100 µm). Furthermore, the interface strength between the coatings and implants are not optimal.

WO 92/13984 describes a process of deposition of bioactive coatings on conductive substrates. An electrolyte cell contains an inert anode and an electrolyte consisting of a aqueous solution of ions of the ceramic, having a pH value of less than 8. The activated conductive substrate is dipped into the electrolyte solution and the potential between the anode and the conductive substrate is chosen such that a ceramic layer is deposited on the conductive substrate based on the pH rise at the boundary between electrolyte and conductive substrate.

A disadvantage of this solution is that the deposition of the layer proceeds only on the surface of the substrate. This means on the one hand that there is no connection that can be mechanically loaded. On the other hand, the coating can be completely resorbed biologically. Furthermore, the coating always consists of three components, $\alpha$- and $\beta$-tricalcium phosphate and components of the chemical formula $Ca_5(PO_4)_{3-x}(CO_3)_x(OH)_{1+x}$ with X=0.2 or less. This means, that the coating is a mixture of these components unlike the composition of bone.

The object of the invention is the coating of metallic implants, preferably of titanium implants or implants made of titanium alloys, with a gradient layer made of calcium phosphate phases and metal oxide phases. Thus, beside the effect of an accellerated ingrowth a permanent improvement of the interaction between implant surface and the biological system can be gained. Moreover, it should be possible to control the composition of the calcium phosphate phases via the process parameters, so that hydroxyapatite, octacalcium phosphate or brushite as well as defined combinations of these phases can be produced alternatively.

According to the invention, the object is realised via an electrochemical process using i) a substrate electrode formed by a metal implant, ii) a counter electrode, iii) an aqueous solution with calcium and phosphate ions being slightly acid or neutral and changing the polarisation of the substrate electrode periodically from cathodic to anodic.

Preferably, the ratio of the concentration of the calcium and phosphate ions is chosen such that it is equal to their concentrations in hydroxyapatite. In a preferred implementation of the invention the electrolyte is produced from an aqueous solution of $CaCl_2$ and $NH_4H_2PO_4$ with a ratio of concentration of calcium and phosphate ions equal that of hydroxyapatite. The pH value is preferably adjusted between 4 and 7.5 by means of a diluted $NH_4OH$ solution. The use of other easily soluble calcium salts and phosphates (for example alkali phosphates) is also possible. Additionally, mainly the conditions of the electrolysis determine the formation of particular calcium phosphate phases and their mixtures, respectively. It is also possible to choose different concentration ratios of calcium and phosphate ions.

In an arrangement consisting of a substrate electrode, reference electrode and counter electrode the substrate electrode formed by the implant is polarised varying the polarisation from cathodic to anodic and vice versa. Preferably, the substrate electrode is polarised cathodically in the first step. In repeating steps anodic and cathodic polarizations are added, preferably finishing the deposition with a cathodic polarization of the substrate electrode.

It is advantageous to raise the time periods of the cathodic and anodic polarizations during the repeating steps and/or to carry out the anodic polarizations with a more and more anodic potential. Cathodic and anodic polarisations of the substrate electrode are carried out one after another with a total cathodic polarization time between 1 and 60 minutes and a total anodic polarization time between 1 and 60 min.

The cathodic polarization can be realized potentiostatically or galvanostatically and the anodic polarization can be done potentiostatically, potentiodynamically or galvanostatically until the desired target potential is reached. The target potential is in the region of 2 to 150 $V_{SCE}$. The choice of the target potential determines the thickness of the titanium oxide layer to build up and therefore the thickness of the gradient region of the coating.

The current density of the cathodic galvanostatic polarization is preferably chosen to be 0.1 to 5 mA/cm².

The three-electrode arrangement for the execution of the process according to the invention is made of a saturated calomel electrode as the reference electrode, a platinum sheet as the counter electrode and the metallic implant as the substrate electrode. A thermostatically controlled cell is used as the electrolyte cell. The electrochemical reaction is carried out preferably at a temperature of 60° C.

With the help of the process described in the invention the desired calcium phosphate phase or the defined mixture of calcium phosphate phases can be build up from the used electrolyte solution as a gradient structure with the metal oxide of the implant material. The coating deposited on the metal implant reduces a good growing of bone towards to the implant supporting the incorporation of the implant into the biological system. Under the influence of substances of the body the coating is normally absorbed. To give the bone an orientation throughout the whole lifetime, calcium phosphate particles are not only fixed to the implant, but included. This is possible because of the step-by-step process of the cathodic and anodic polarization of the substrate electrode. The desired calcium phosphate phase or mixture of phases is deposited on this substrate electrode from the electrolyte during the cathodic polarization. During the anodic polarization the oxide layer of the implant metal begins to grow over the deposited calcium phosphate particles, resulting in an incorporation into the oxide layer of the metal. Repeating these steps, the thickness of the layer is increased. For the growth of the layer it is advantageous to raise the time periods of the steps and to carry out the second step with a more and more anodic potential. To obtain a surface layer of calcium phosphate phases, finishing the process of making the gradient layer with a cathodic polarization is advantageous.

The advantage of the deposited layers according to the invention is a better transmission of forces and a permanent improvement of biocompatibility by means of the incorporation of calcium phosphate phases in the implant surface. With the possibility of adaption of the composition of the layer to the composition of the inorganic bone substance a quick ingrowth of bone is supported.

The invention is explained in more detail with the following examples:

EXAMPLE 1

A disc made of 99.7% pure titanium and a diameter of 13 mm, a thickness of 2 mm is ground, cleaned in alcohol, rinsed in deionized water and dried with a fan. As electrolyte solution a calcium phosphate solution is used, produced as follows: 10 ml stock solution of $CaCl_2 \cdot 2H_2O$ and $NH_4H_2PO_4$, in concentrations of 33 mM and 20 mM respectively are diluted and mixed, resulting in 200 ml of 1.67 mM calcium and 1.0 mM phosphate. Before, the pH value is adjusted with a diluted $NH_4OH$ solution to 6.4. The solution is heated to 60° C. and poured into a double jacket cell. A three-electrode arrangement is set up. A saturated calomel electrode is used as a reference electrode. Counter electrode is a platinum sheet. The titanium disc forms the working electrode. After this the potentiostat is contacted. The formation of the hydroxyapatite layer is realized through a varying polarization:

10 min cathodic polarization of the titanium sample, galvanostatic with I=1 mA ($1^{st}$ step).

10 min anodic polarization, potentiostatic with U=5 $V_{SCE}$ ($2^{nd}$ step)

15 min cathodic polarization according to step 1 ($3^{rd}$ step)

10 min anodic polarization with U=10 $V_{SCE}$ ($4^{th}$ step)

finishing with 35 min of cathodic polarization according to the $1^{st}$ step ($5^{th}$ step).

The sample is removed from the electrolyte, rinsed with deionized water and dried with a fan. The deposited layer looks whitish yellow, is uniformly developed and has a good interface bonding. Investigations carried out with an scanning electron microscope revealed a closed coating, consisting of agglomerates of very fine needles having a length of about 500 nm. Analysis of the element composition by means of energy dispersive X-ray analysis gave a Ca/P ratio of the phase in the coating equal to that of commercial hydroxyapatite. X-ray diffraction analysis verified the phase to be hydroxyapatite.

The wedge-shaped preparation shows a gradient structure of the coating. Under the scanning electron microscope no sharp transition between substrate and coating can be seen.

EXAMPLE 2

An electrolyte identical to that of example 1 is used. The titanium disc is prepared according to example 1. The electrochemical setting is equal to example 1. After a galvanostatic, cathodic polarization (I=0.3 mA, 10 min) ($1^{st}$ step) starting with the potential, set up by the process of the galvanostatic, cathodic polarization, in the $2^{nd}$ step polarization is carried out anodically at polarizing speed of 5 mV/s until a level of 5 $V_{SCE}$ is reached. After reaching this potential a cathodic polarization with 0.3 mA is carried out in step 3. Starting with the potential, set up by the process of the galvanostatic, cathodic polarization the $4^{th}$ step is an anodic polarization with a speed of 5 mV/s until 10 $V_{SCE}$ is reached. The process is finished with a cathodic polarization 35 min according to the $1^{st}$ step ($5^{th}$ step).

The coating on the substrate electrode consists of octacalcium phosphate. Electron microscopical investigations show crystals with shapes from needels to bands with dimensions up to 5 μm. Comparisons, done by X-ray diffractometric and raman spectroscopic analyses show that the coating is made of octacalcium phosphate.

The wedge-shaped preparation shows a gradient transition in the phase boundary. Under the scanning electron microscope no sharp transition between substrate and coating can be seen.

EXAMPLE 3

A titanium disc is prepared according to example 1. 200 ml of a calciumphoshpate solution is used as an electrolyte solution with the following composition realized by weighing in the salts: 40 mM $CaCl_2$ and 25 mM $NH_4H_2PO_4$. The pH-value is set to 4.4.

The electrochemical arrangement is equal to example 1.

After the first potentiostatic cathodic polarization with $U_{SCE}$=−1300 mV, 10 min (step 1 ) the electrode is polarized galvanostatic anodic in a second step 10 min with 1 mA. After 15 min of cathodic polarization according to step 1 ($3^{rd}$ step) galvanostatic anodic polarization is done in a $4^{th}$ step 10 min with 2 mA. The process is finished with a cathodic polarization 35 min according to step 1 ($5^{th}$ step).

The coating on the substrate electrode consists of cristals with shapes of of little plates and a dimension up to 30 μm.

Energy dispersive X-ray analysis gives a Ca/P ratio of the phase in the coating equal to that of commercial brushite. X-ray diffraction revealing the crystal structure establishes that the phase is hydroxyapatite.

The wedge-shaped preparation shows a gradient transition in the phase boundary. Under the scanning electron microscope no sharp transition between substrate and coating can be seen.

EXAMPLE 4

An electrolyte identical to the one of example 1 is used. The titanium disc is produced according to example 1 and additionally polished until a reflecting surface is gained and etched oxidising in 50 ml of a solution, consisting of 0.5 M NaOH and 0.1 M $H_2O_2$ for 4 min at a temperature of 65° C. The etched surface shows a varying corrosion of the titanium crystals under the electron microscope. Deposition of the coating takes place in the same way as in example 1. Electron microscopic analysis shows the needle like crystals as in example 1 with the Ca/P ratio of hydroxyapatite. All in all the coating has higher roughness. The coating shows a better interface bonding to the substrate than in example 1. The investigated wedge-shaped cut shows additionally to the graduated transition an interlocking between substrate and coating.

We claim:

1. A process for producing a gradient coating of calcium phosphate phases and metal oxide phases on a metal implant, comprising:

provide a metal implant;

providing an electrolyte solution containing calcium phosphate ions, and having a pH of between 4.0 and 7.5;

providing a counter electrode in the electrolyte solution;

placing the implant in the electrolyte solution;

applying an electrical potential between the counter electrode and the implant, so that the implant initially acts as a substrate cathode;

periodically reversing the polarity of the electrical potential a plurality of times, so that the implant alternates between cathodic polarization and anodic polarization, to deposit a gradient coating of calcium phosphate phases and metal oxide phases on the implant.

2. A process according to claim 1, wherein the ratio of calcium to phosphate ions in the electrolyte is equal to that of hydroxyapatite.

3. A process according to claim 1, wherein the deposition is halted after a cathodic polarization step.

4. A process according to claim 1, wherein the time period of polarization is raised for at least one step after the initial polarization.

5. A process according to claim 1, wherein the anodic polarization is carried out with increasingly positive potential.

6. A process according to claim 1, wherein the cathodic polarization is carried out potentiostatically or galvanostatically and the anodic polarization is carried out potentiodynamically or galvanostatically until a target potential of between 2 and 150 $V_{SCE}$ is reached.

7. A process according to claim 1, wherein the total time of anodic polarization is between 1 and 60 minutes, and the total time of cathodic polarization is between 1 and 60 minutes.

8. A process according to claim 1, wherein the cathodic polarization is galvanostatic, and is carried out at a current density of between 0.1 and 5 mA/cm$^2$.

9. A process according to claim 1, wherein each period of polarization lasts at least 10 minutes.

* * * * *